United States Patent [19]
Lattrell et al.

[11] Patent Number: 4,845,087
[45] Date of Patent: Jul. 4, 1989

[54] CRYSTALLIZED CEPHEM-ACID ADDITION SALTS, AND A PROCESS FOR THE PREPARATION THEREOF

[75] Inventors: Rudolf Lattrell, Königstein/Taunus; Walter Dürckheimer, Hattersheim am Main; Reiner Kirrstetter, Kelkheim, all of Fed. Rep. of Germany

[73] Assignee: Hoechst Aktiengesellschaft, Frankfurt am Main, Fed. Rep. of Germany

[21] Appl. No.: 159,395

[22] Filed: Feb. 23, 1988

[30] Foreign Application Priority Data

Feb. 25, 1987 [DE] Fed. Rep. of Germany ....... 3706020

[51] Int. Cl.$^4$ ................. C07D 501/46; A61K 31/545
[52] U.S. Cl. .................................... 514/202; 540/222
[58] Field of Search ................. 540/222, 225; 514/225

[56] References Cited
U.S. PATENT DOCUMENTS
4,667,028 5/1987 Schwab et al. ..................... 540/225

OTHER PUBLICATIONS
The Merck Index, pp. 1896 and 1897, (1983, Tenth Edition).

Primary Examiner—Nicholas S. Rizzo
Attorney, Agent, or Firm—Finnegan, Henderson, Farabow, Garrett, & Dunner

[57] ABSTRACT

Crystallized cephem-acid addition salts of the general formula

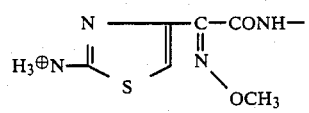

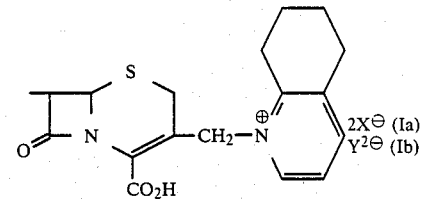

pharmaceutical preparations which contain such cephem derivatives and are active against bacterial infections, a process for the preparation of the cephem derivatives and the pharmaceutical preparations, and the use of the cephem derivatives for combating bacterial infections.

4 Claims, No Drawings

CRYSTALLIZED CEPHEM-ACID ADDITION SALTS, AND A PROCESS FOR THE PREPARATION THEREOF

DESCRIPTION

The invention relates to crystallized acid-addition salts of an antibiotic of the formula Ia or Ib and the hydrates thereof, and a process for the preparation of these compounds.

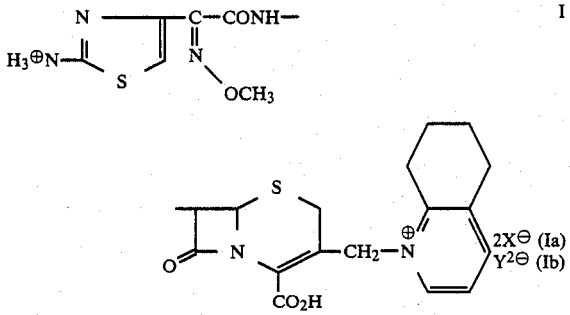

In the general formula I,
$X^-$ denotes the anion of a monobasic acid, and
$Y^{2-}$ denotes the anion of a dibasic acid, where X and Y may be an inorganic or organic anion.

As an inorganic anion, $X^-$ or $Y^{2-}$ denotes, for example, $Cl^-$, $Br^-$, $I^-$, $F^-$, $NO_3-$, $ClO_4-$, $SCN^-$ or $HSO_4-$, in particular physiologically acceptable anions such as, for example, $Cl^-$, $Br^-$, $HSO_4-$ and $SO_4--$. As an organic anion, $X^-$ is the anion of an aliphatic mono-, di- or tricarboxylic acid, for example $CH_3CO_2-$, $CF_3CO_2-$ or $CCl_3CO_2-$, in particular the anion of a physiologically acceptable acid, such as, for example, the monomaleate anion $HOOCCH=CHCO_2-$.

The sulfate, which is distinguished by a very low tendency towards incorporation of organic solvents into the crystal lattice, is very particularly suitable for parenteral administration. The dihydroiodide is particularly suitable for isolation of the betaine of the formula II from the reaction batches.

The process for the preparation of the acid-addition salts of the formulae Ia and Ib comprise
(1) reacting a cephem-betaine of the formula II

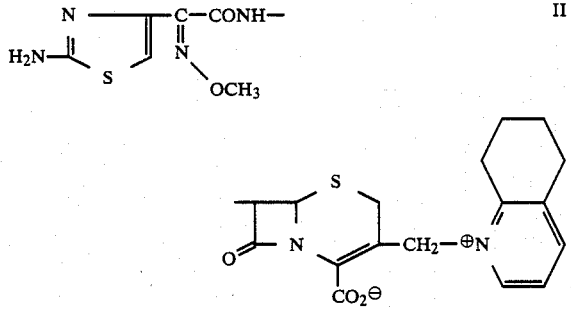

with monobasic acids of the formula IIIa or dibasic acids of the formula IIIb $H^+X^-$     IIIa $2H^+Y^{2-}$   IIIb in which X and Y have the abovementioned meaning, or
(2) reacting a cephem-betaine of the formula II with acids of the formula IIIa or IIIb which have been produced in situ, these acids being produced from the corresponding salts of the formula IVa or IVb respectively ZX or $ZX_2$     IVa $Z_2Y$ or ZY    IVb in which Z denotes a monovalent or divalent metal cation, for example $Na^+$, $K^+$, $Ag^+$ or $Mg^{2+}$, or an ammonium ion, through addition of a strong acid, such as, for example, the mineral acids HCl and $H_2SO_4$, or
(3) preparing a water-soluble salt of the formula I, for example a dihydrochloride or sulfate, in accordance with process 1 and reacting this salt with salts of the formula IVa or IVb in which $X^-$ and $Y^{2-}$ denote the anion of a sparingly water-soluble salt, for example $I^-$.

The preparation of the betaine of the formula II on which the salts of the general formula I according to the invention are based is described in European Pat. No. 0,064,740 (Example 51).

In accordance with process 1, a monobasic or dibasic acid of the formula IIIa or IIIb is added to a solution of the compound II in water or in a mixture of water and a water-miscible organic solvent, such as, for example, methanol, ethanol, isopropanol, acetone, tetrahydrofuran or acetonitrile. The acids $H^+X^-$ and $2H^+Y^{2-}$ can be added as solids or in solution, for example in water or in water-miscible, abovementioned organic solvents, or in mixtures of water and these solvents.

The formation of the salts of the formulae Ia and Ib is carried out at temperatures between $-20°$ and $+80°$ C., preferably between $-5°$ and $+30°$ C. The salts crystallize spontaneously on standing, while stirring or after seeding, or by precipitation by means of a solvent such as acetone or ethanol.

The acid of the formula III must be added in at least twice the equimolar amount, but it is also possible to employ an excess.

After addition of the acid III, a solution forms initially which can be filtered, it possibly being advantageous in some cases to clarify the solution using activated charcoal before filtration.

The process can also be carried out by adding the cephem base II, directly or dissolved in water, to a solution of the acid III.

The starting compound of the formula II can also be liberated from its salts by treatment with a basic ion exchanger, for example the solid exchanger Amberlite IRA 93 or the liquid exchanger Amberlite LA-2, in aqueous solution, and then converted into an acid-addition salt as described above.

In accordance with process 2, the salt of the formula IVa or IVb is added in at least twice the equimolar amount up to a ten-fold excess to the solution of the compound II, and the fundamental acid $H^+X^-$ or $2H^+Y^{2-}$ is liberated by adding a strong mineral acid, such as, for example, HCl or $H_2SO_4$.

In this way, the corresponding sparingly soluble salts can be prepared using acids, for example from HI or HSCN produced in situ.

In accordance with process 3, a salt of the formula IVa or IVb whose fundamental anion forms a sparingly soluble acid-addition salt with the compound II, for example the dihydroiodide or dihydroperchlorate of the compound II, is added to the solution of a salt Ia or Ib in water. The reaction and crystallization are carried out as described for process 1.

The compounds of the formulae Ia and Ib obtained in accordance with the process described above are isolated, for example, by filtration or centrifugation and are dried at atmospheric pressure or in vacuo, expediently with the aid of a dehydrating agent, such as, for example, concentrated sulfuric acid or phosphorus pentoxide. Depending on the drying conditions, the compound of the formula I is produced here as the hydrate or in anhydrous form.

The compounds of the general formula I obtained according to the invention exhibit remarkably good antibacterial activities, both against Gram-positive and Gram-negative bacterial germs.

The compounds of the formula I are also unexpectedly highly active against penicillinase- and cephalosporinase-forming bacteria. Since, in addition, they exhibit favorable toxicological and pharmacological properties, they represent valuable chemotherapeutic agents.

The invention thus also relates to medicament preparations for treatment of microbial infections in mammals (both in humans and in animals), which preparations are characterized in that they contain one or more compounds according to the invention, in particular the physiologically acceptable acid-addition salts.

The products according to the invention can also be used in combination with other active compounds, for example from the series comprising the penicillins, cephalosporins or aminoglycosides.

The compounds of the general formula I can be administered subcutaneously, intramuscularly, interarterially or intravenously, and also intratracheally or locally in animals, such as, for example, into the udder of milk-giving animals.

Medicament preparations which contain one or more compounds of the general formula I as active compound can be produced by mixing the compounds of the formula I with one or more pharmacologically acceptable excipients or diluents, such as, for example, buffer substances, and converted into a formulation which is suitable for parenteral administration.

Diluents which may be mentioned are, for example, polyglycols, ethanol and water. Buffer substances are, for example, organic compounds, such as, for example, N',N'-dibenzylethylenediamine, diethanolamine, ethylenediamine, N-methylglucamine, N-benzylphenethylamine, diethylamine or tris(hydroxymethyl)aminomethane, or inorganic compounds, such as, for example, phosphate buffer, sodium bicarbonate or sodium carbonate. Suspensions or solutions in water, with or without buffer substances, are preferably possible for parenteral administration.

Suitable doses of compounds of the general formula I are about 0.4 to 20 g/day in the case of administration to humans, preferably 0.5 to 4 g/day for an adult of approximate body weight 60 kg.

Single or in general multiple doses can be administered, it being possible for the individual dose to contain the active compound in an amount of about 50 to 1000 mg, preferably from about 1200 to 500 mg.

In the case of administration to animals, all mammals are possible in principle, in particular pets and useful animals in view of their importance. The dosage varies in the individual species of animal and can be, for example, between about 2.5 and 150, preferably between 5 and 50, mg/kg of body weight of the animal.

It was surprising that the crystalline acid-addition products obtained according to the invention would have an unexpectedly large increase in stability compared both to betaine and to corresponding amorphous salts. Thus, for example, the activity is virtually retained in the crystalline sulfate on heating for several weeks, whereas it exhibits a large decrease in the other product forms mentioned above. Due to the unexpectedly good properties of the final products, the formulations produced using them have a far better purity and safety on therapeutic use.

The following illustrative embodiments for acid-addition compounds, which can be prepared according to the invention, of the compound II, 1-[[(6R,7R)(Z)-[[2-(2-amino-4-thiazolyl)(methoxyimino)acetyl)amino]-2-carboxy-8-oxo-5-thia-1-azabicyclo[4,2,0]-oct-2-en-3-yl]methyl]-5,6,7,8-tetrahydroquinolinium hydroxide, internal salt, serve to further illustrate the invention, but do not represent a limitation.

EXAMPLE 1

Sulfate of the compound II (process 1)

A mixture of 8.2 (0.01 mol) of the dihydroiodide salt of the compound II (Example 2a), 15 ml of Amberlite LA-2 (Serva 40610), 30 ml of water and 50 ml of EtOAc is stirred at 20° C. for 30 minutes. After 15 minutes, the dihydroiodide salt has dissolved. The phases are separated and the aqueous phase is washed with 50 ml of toluene. After addition of 0.6 g of animal charcoal, the aqueous phase, which contains the betaine II, is stirred for 15 minutes, filtered, cooled to 10° C. and acidified to pH 1.3 using 6N sulfuric acid. 60 ml of cold ethanol are then added while stirring. After a short time, crystallization of the sulfate commences. The suspension is stirred at 5° C. for 4 hours and filtered, and the precipitate is washed twice with 15 ml of ethanol in each case and dried in vacuo over $P_2O_5$ to constant weight. Yield: 5.2 g (80.7%) of colorless crystals, decomp. 182° C.

$C_{23}H_{24}N_6O_5S_2 \times H_2SO_4 \times H_2O$ (644.7): calc.: C 42.8 H 4.4 N 13.1 S 14.9 $H_2O$ 2.8%. found: C 42.6 H 4.2 N 13.0 S 14.7 $H_2O$ 3.1%.

EXAMPLE 2

Dihydroiodide of the compound (a) Isolation of II from reaction batches 22.6 g (0.17 mol) of 5,6,7,8-tetrahydroquinoline are added dropwise while stirring to a solution, cooled to 5° C., of 28 g (0.14 mol) of trimethyliodosilane in 200 ml of dichloromethane. 9.1 g (0.02 mol) of 7-[2-(2-aminothiazol-4-yl)-2-(Z)-methoxyiminoacetamido]cephalosporanic acid are then introduced into the stirred solution. The mixture is refluxed for 2 hours, then cooled to 5° C. and hydrolyzed while adding dropwise 60 ml of a mixture of 57 percent strength hydroiodic acid:water:ethanol (1:4:8). The dihydroiodide salt precipitates as a pale yellow precipitate. After 4 hours at 0° C., the mixture is filtered, and the precipitate is washed with 100 ml of methylene chloride and 100 ml of acetone and dried in air. Yield: 13 g (79.2%) of pale yellow crystals, decomp. >200° C.

$C_{23}H_{24}N_6O_5S_2 \times 2HI \times 2H_2O$ (820.5): calc.: C 33.7 H 3.7 N 10.2 S 7.8 I 30.9 $H_2O$ 4.3%. found: C 32.5 H 3.6 N 9.8 S 7.3 I 30.5 $H_2O$ 3.8%.

(b) Dihydroiodide of the compound II (process 1)

25 ml of 1N aqueous hydroiodic acid are added to a solution of 0.01 mol of II, prepared in accordance with Example 1. A yellow precipitate forms immediately, and is filtered off under suction, washed with water and dried. The compound is identical in all properties to the compound described above.

(c) Dihydroiodide of the compound II (process 3)

6.45 g (0.01 mol) of the sulfate (Example 1) are dissolved in 200 ml of water, and a solution of 5.5 g (0.035 mol) of potassium iodide in 5 ml of water is then added. Crystallization of the pale yellow dihydroiodide salt commences after a short time. After 2 hours, the precipitate is filtered off under suction, washed with water and dried. The compound is identical in all properties to the compound described above.

EXAMPLE 3

Dihydrothiocyanate of the compound II (process 2)

6 ml of 1N HCl are added to a solution of 1.06 g (2 mmol) of II and 0.58 g (6 mmol) of potassium rhodanide in 6 ml of water while shaking. The crystal suspension formed is stirred at 10° C. for 2 hours, and the precipitate is filtered off under suction and washed twice with 5 ml of ice water in each case. After drying over $P_2O_5$ in vacuo, 0.78 g (59% of theory) of colorless crystals, decomp. 166° C., is obtained.

$C_{23}H_{24}N_6O_3S_2 \times 2HSCN \times H_2O$ (664.8): calc.: C 45.2 H 4.3 N 16.9 S 19.3 $H_2O$ 2.7%. found: C 45.0 H 4.4 N 16.5 S 18.3 $H_2O$ 1.5%.

EXAMPLE 4

Dihydronitrate of the compound II (process 1)

5 ml of 1N nitric acid are added to the solution of 1.06 g (2 mmol) of II in 6 ml of water while shaking. The crystalline precipitate formed is filtered off under suction, washed twice with 3 ml of ice water in each case and dried over $P_2O_5$. Yield: 0.92 g (67% of theory) of colorless crystals, decomp. >140° C.

$C_{23}H_{24}N_6O_5S_2 \times 2HNO_3 \times H_2O$ (672.7): calc.: C 41.1 H 4.2 N 16.7 S 9.5 $H_2O$ 2.7%. found: C 40.9 H 4.1 N 16.6 S 9.3 $H_2O$ 2.7%.

EXAMPLE 5

Dihydroperchlorate of the compound II (process 1)

5 ml of 1N perchloric acid are added to the solution of 1.06 g (2 mmol) of II in 6 ml of water. The precipitate formed is filtered off under suction, washed three times with 3 ml of water in each case and dried over $P_2O_5$ in vacuo. Yield: 1.2 g (80%) of colorless crystals, decomp. >160° C.

$C_{23}H_{24}N_6O_5S_2 \times 2HClO_4 \times H_2O$ (747.6): calc.: C 37.0 H 3.8 Cl 9.5 N 11.2 S 8.6 $H_2O$ 2.4%. found: C 36.8 H 3.8 Cl 10.1 N 11.8 S 8.6 $H_2O$ 2.8%.

EXAMPLE 6

Dihydrotetrafluoroborate of the compound II (process 1)

5 ml of 1N tetrafluoroboric acid are added to the solution of 1.06 g (2 mmol) of II in 6 ml of water. After the mixture has been standing for 1 hour in an ice bath, the precipitate formed is filtered off under suction, washed with 2 ml of ice water and dried over $P_2O_5$. Yield: 0.85 g (59%) of colorless crystals, decomp. 178° C.

$C_{23}H_{24}N_6O_5S_2 \times 2HBF_4 \times H_2O$ (722.3): calc.: C 38.3 H 3.9 F 21.0 N 11.6 S 8.9 $H_2O$ 2.5%. found: C 38.5 H 4.1 F 20.3 N 11.4 S 8.6 $H_2O$ 2.8%.

EXAMPLE 7

Dihydrobromide of the compound II (process 1)

1 ml of 4N hydrobromic acid is added to the solution of 1.06 g (2 mmol) of II in 6 ml of water. After the mixture has been standing for 4 hours in an ice bath, the precipitate formed is filtered off under suction, washed with 1 ml of ice water and dried over $P_2O_5$. Yield: 0.11 g (75%) of colorless crystals, decomp. 188° C.

$C_{23}H_{24}N_6O_5S_2 \times 2HBr \times H_2O$ (708.5): calc.: C 39.0 H 4.0 Br 22.6 N 11.9 S 9.1 $H_2O$ 2.6%. found: C 38.5 H 3.8 Br 21.8 N 11.6 S 8.9 $H_2O$ 2.9%.

EXAMPLE 8

Dihydrochloride of the compound II (process 1)

A solution of 1.06 g (2 mmol) of II in 6 ml of water is acidified to pH 1.3 using concentrated hydrochloric acid. After some time, a precipitate deposits out of the solution.

After standing for 24 hours at 0° C., the precipitate is filtered off under suction and dried over $P_2O_5$. Yield: 0.2 g (16%) of colorless crystals, decomp. 190° C. 20 ml of ethanol are added to the mother liquor, the mixture is concentrated in vacuo, and a further 6 ml of ethanol are added to the concentrated solution (3 ml). The solution is decanted from a little resin. After standing for a relatively long period, a second crystal fraction deposits out of the solution, and is filtered off under suction and dried over $P_2O_5$. Yield: 0.3 g (24%) of colorless product, decomp. >180° C.

$C_{23}H_{24}N_6O_5S_2 \times 2HCl \times H_2O$ (619.5): calc.: C 44.6 H 4.6 Cl 11.4 N 13.6 S 10.3 $H_2O$ 2.9%. found: C 44.1 H 4.7 Cl 11.6 N 13.4 S 10.0 $H_2O$ 3.3%.

EXAMPLE 9

Dihydromaleate of the compound II (process 1)

18 ml of acetone are added to a solution of 1.06 g (2 mmol) of II and 0.58 g (5 mmol) of maleic acid in 6 ml of water. A slight turbidity is removed by filtration. After standing overnight at 0° C., a colorless product crystallizes from the solution. The product is filtered off under suction, washed three times with 10 ml of acetone in each case and dried over $P_2O_5$. Yield: 1.0 g (63%) of colorless crystals, decomp. 135°–140° C.

$C_{23}H_{24}N_6O_5S_2 \times C_8H_8O_8 \times H_2O$ (796.8): calc.: C 46.7 H 4.3 N 10.5 S 8.0 $H_2O$ 2.3%. found: C 46.9 H 4.5 N 10.8 S 8.2 $H_2O$ 2.2%.

We claim:

1. A crystalline cephem-acid addition salt of the formula I

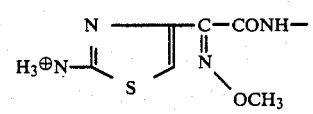

-continued

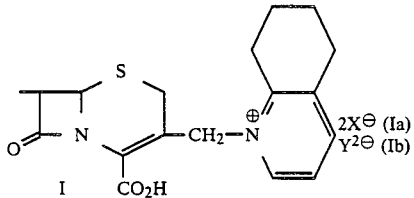

in which X⁻ represents an iodide, thiocyanate, nitrate, perchlorate, tetrafluoroborate, bromide, chloride or hydromaleate anion in formula Ia and Y²⁻ represents a sulfate anion in formula Ib or the hydrate thereof.

2. A dry non-liquid pharmaceutical composition which is effective against bacterial infections in mammals, which contains an effective antibacterial amount of the crystalline cephem compounds of formula I as defined in claim 1.

3. A dry non-liquid pharmaceutical composition comprising an effective antibacterial amount of the crystalline cephem compounds of formula I as defined in claim 1 in combination with a pharmaceutically acceptable excipient, diluent or buffer substance.

4. A method of treating bacterial infections in mammals which comprises administering an effective amount of a crystalline cephem compound of the formula I as defined in claim 1.

* * * * *